(12) United States Patent
Couvreur

(10) Patent No.: US 6,341,607 B1
(45) Date of Patent: Jan. 29, 2002

(54) FEMALE CONDOM

(75) Inventor: Chantal Couvreur, Belgium (BE)

(73) Assignee: Mediteam SPRL, Brussels (BE)

( * ) Notice: Subject to any disclaimer, the term of this patent is extended or adjusted under 35 U.S.C. 154(b) by 0 days.

(21) Appl. No.: 09/367,626

(22) PCT Filed: Feb. 6, 1998

(86) PCT No.: PCT/EP98/00642

§ 371 Date: Dec. 6, 1999

§ 102(e) Date: Dec. 6, 1999

(87) PCT Pub. No.: WO98/36716

PCT Pub. Date: Aug. 27, 1998

(30) Foreign Application Priority Data

Feb. 19, 1997 (LU) .................................................. 90030

(51) Int. Cl.$^7$ .................................................. A61F 6/04
(52) U.S. Cl. ........................ 128/844; 128/842; 128/830; 128/918
(58) Field of Search ................. 128/842, 844, 128/918; 604/347–353

(56) References Cited

U.S. PATENT DOCUMENTS

| 4,840,624 | A | | 6/1989 | Lee | |
|---|---|---|---|---|---|
| 5,113,873 | A | * | 5/1992 | Boarman | 128/830 |
| 5,163,449 | A | * | 11/1992 | Valk | 128/844 |
| 5,325,871 | A | | 7/1994 | Reddy | |
| 5,490,525 | A | * | 2/1996 | Reddy | 128/844 |
| 6,035,853 | A | * | 3/2000 | Alla | 128/844 |

FOREIGN PATENT DOCUMENTS

| FR | 2 730 920 | 8/1996 |
|---|---|---|
| WO | WO 88 06432 | 9/1988 |

* cited by examiner

*Primary Examiner*—Michael A. Brown
(74) *Attorney, Agent, or Firm*—Smith, Gambrell & Russell, LLP

(57) ABSTRACT

The invention concerns a female condom (10) for protection against sexually transmissible diseases to be inserted in a user's vagina, comprising a thin-walled flexible tube (15) with a closed end (20) and an open end (25), said open end provided with means for being radially stretched comprising a flexible collar (35) made in harder material than the thin flexible tube (15) and extending perpendicular to said tube so as to cover the vulva during intercourse.

43 Claims, 1 Drawing Sheet

U.S. Patent
Jan. 29, 2002
US 6,341,607 B1
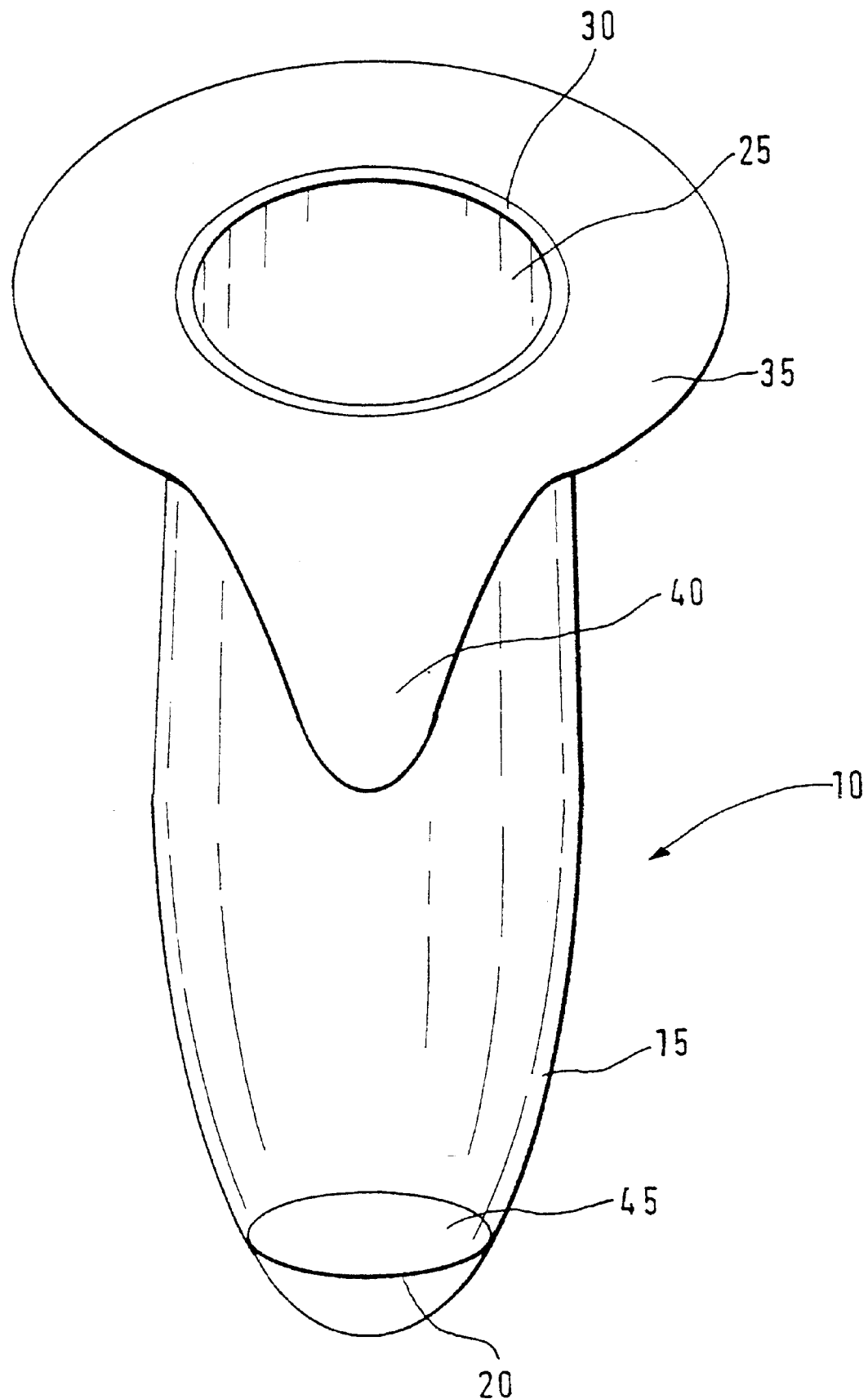

FEMALE CONDOM

Although campaigns for the prevention of AIDS recommend the use of condoms, a good proportion of the most exposed populations do not use them. These are mainly:
- young;
- couples in which man is not able to experience same degree of sexual pleasure with a condom;
- couples in which an unfaithful partner cannot suddenly ask for a condom to be used without raising suspicions;
- prostitutes having certain clients who refuse to use a condom for various reasons.

While the incidence of AIDS among homosexuals and bisexual men has been observed to stabilise, the proportion of the heterosexual population infected is still increasing- most of these cases arise from indulgence in sexual relations without taking precautions.

During the XI International Conference on AIDS (Vancouver 1996), a Brazilian delegate showed that the use of the traditional male condom, even when the woman wanted it, was often rendered impossible by the refusal of the partner (R. Loureiro, Condom use among young women of the urban poor population, who attend a public hospital of Porto Alegre, Brazil, XI International Conference on AIDS, Vancouver Jul. 7–12, 1996, Th. C. 4483, pp 329–330), and a group of researchers at the Harvard Medical School and the World Health Organisation considered that the use of a female condom gave women a greater freedom to negotiate sexual relations without risks (A. Purohit, H. Tamashiro, J. Steinberg, A. Kiessling and J. Chakraborty, Prevention issues of male and female condoms, XI International Conference on AIDS, Vancouver Jul. 7–12, 1996, Th. C. 4464, p 327).

Moreover, it is known that women are more vulnerable to AIDS and other sexually transmitted diseases than men.

That is why the European Commission report on the state of women's health in the European Union (1996) considers that, since women are more vulnerable than men in contracting this disease, "it is upon women that efforts should be focused in preventing the propagation of this fatal disease" (Report on the state of women's health in the European Community, Commission of the European Communities 1996).

In addition, it is known that women are usually better agents of prevention.

There are some female condoms currently on the market. EP 0 280 943 describes a female condom consisting of a tubular device for protection against sexually transmitted diseases which can be inserted in the vagina of a user. The female condom comprises a flexible thin-walled tube with a closed end and an open end. The open end has means for stretching it radially, thus preventing the tube from collapsing and keeping the opening open.

One of the disadvantages of such a female condom is that there is a relatively high risk of penetration outside the condom, particularly with repeated contacts.

FR.A.2 730 920 describes a prefitted prophylactic device which is self-introduced on penetration. The device consists of a retentive sheath, generally tapered in shape, which is closed at its smaller end by a spherical cap, the other end being open. The open end has a support plate attached firmly to it, the said plate having an opening with a perimeter equal to that of the open end. The plate is strong, so that it is capable of keeping the opening in the said sheath roughly circular, while remaining flexible. The whole device is intended, through the intermediary of the support plate, to be joined to a textile medium such as an item of underwear.

The aim of the present invention is to propose a female condom that reduces the risk of penetration outside the female condom during coitus.

For this purpose, the invention proposes a female condom comprising a flexible thin-walled tube having a closed end and an open end, the open end having means for stretching the open end radially, the said means for stretching the said open end radially comprising a collarette made of a material harder to the touch than the flexible thin tube, extending in a direction perpendicular to the tube in such a way as to cover the vulva during coitus, characterised in that the collarette has a protuberance elongated in the direction of the anus. It thus covers the region lying between the vulva and the anus during coitus.

For a female condom to be an effective barrier to the transmission of the AIDS virus or other viruses and microbes, it is essential that, even during repeated contacts, the penis is unable to penetrate the vagina outside the condom. That is why it is advantageous to provide a female condom in which the collarette comprises a protuberance or tongue elongated towards the anus and placed parallel to the vulva and perpendicular to the tubular part of the condom.

The collarette, complete with its tongue covering the woman's vulva, holds the open end of the female condom in place and is an effective barrier to the transmission of diseases since contact between the bodily fluids of the man and the woman is prevented. The collarette, fitted with the tongue made of a material harder to the touch, enables the man to determine the position of the entrance to the female condom and thus to reduce the risk of penetration outside the condom.

In a case of penetration outside the female condom, the fact that the collarette is made of a material harder to the touch enables the partners to appreciate the problem immediately. This is a considerable advantage compared with known female condoms lacking a collarette harder to the touch, condoms for which the penis has to be guided into the tube and with which the partners do not realise anything in a case of penetration outside the condom.

According to a first advantageous embodiment, the means for stretching the open end radially comprises a ring with roughly the same diameter as the tube and delimiting the collarette with respect to the tube. The open end of the tube is kept open using, for example, a plastic ring which has on its perimeter a collarette made of a material harder to the touch than the thin flexible tube.

Preferably, the ring has a diameter identical to that of a vagina. This ring may, according to another embodiment, slide over the said tube.

Advantageously, the collarette is made from a more rigid material and/or a thicker material than the thin flexible tube.

In a preferred embodiment of the invention, the length of the flexible thin-walled tube is chosen so that the collarette is maintained in contact with the vulva. With a view to increasing the comfort of the female condom, it is preferable for the collarette to be maintained permanently pressed against the lips of the vagina. As the vagina may have various sizes, it is preferable to make available female condoms of different lengths. It might also be possible to provide different widths of collarette.

In another advantageous embodiment, the said closed end incorporates a means for retention enabling the female condom to be held inside the vagina during sexual intercourse.

Preferably, the means for retention is a ring made of a semi-rigid material or of foam rubber. The said means for retention may be impregnated with a spermicidal and/or antiseptic substance.

For those particularly exposed to the virus (seropositive partner), a diaphragm placed inside the tubular part or a thin foam rubber disc could avoid the risk of perforating the condom.

For those less exposed to this risk, a hollowed-out foam rubber ring or disc or a semi-rigid ring could be enough to keep the condom inside the vagina during sexual intercourse.

According to another advantageous embodiment, the said means for retention is capable of being inserted in the closed end in such a way that it can be removed.

The female condom may also incorporate a means for fixing the means for retention to the thin-walled tube.

Advantageously, the flexible thin-walled tube is made from a polymeric material such as natural rubber latex (NRL), polyethylene, polyurethane and derivatives and mixtures of these materials. The female condom may be lubricated inside and/or outside with a lubricant sufficient to improve the comfort.

Other characteristics of the invention are described, in a non-limiting way, in the examples and in relation to the figure which shows a female condom.

The female condom 10 capable of being inserted into the vagina of a user comprises a flexible thin-walled tube 15 having a closed end 20 and an open end 25. The open end 25 is provided with a ring 30 which has roughly the same diameter as the said tube 15 and which delimits the collarette 35 with respect to the tube 15. The open end 25 of the tube 15 is kept open with the help of this plastic ring 30, which carries on its outer circumference the collarette 35 made of a material harder to the touch than the thin flexible tube. The collarette 35 extends in a direction perpendicular to the said tube 15 so as to cover the vulva during coitus. The female condom 15 also offers good protection against the transmission of sexually transmitted diseases as well as efficient protection against unintentional pregnancies. The collarette, because it covers the vulva and reduces the risk of penetration outside the condom, makes the female condom safer than a standard male condom. Unlike known female condoms, the present female condom incorporates a ring between the collarette and the tube. This ring reduces still further the risk of unintentional penetration outside the condom. The female condom is held in position inside the vagina during coitus, and similarly the collarette generally remains in position.

The thickness of the tube and the collarette may vary, it being understood that greater thicknesses of the wall and collarette reduce sensitivity during coitus. Typical thickness for the tube lie between 20 and 100 micrometres, while the collarette may be thicker.

Of course, the thickness of the wall must be such that the resistance to mechanical stresses of the female condom laid down by standards in force in different countries is guaranteed. The dimensions of the female condom are such that they allow movement of the penis relative to the female condom during sexual intercourse.

The collarette 35 has a protuberance or tongue 40 elongated towards the anus, which is placed parallel to the vulva and perpendicular to the tubular part of the condom. The tongue 40 covers the region lying between the vulva and the anus of the user during coitus.

The female condom 10 may be produced in different lengths, i.e. the length of the tube 15 may be different depending on the size of the user's vagina, so that for each user the collarette 35 is maintained in contact with the vulva. In general, the width of the collarette 35 lies between 1 and 4 cm and preferably between 1and 2 cm. Of course, the width of the collarette 35 need not necessarily be uniform over the whole of its perimeter.

The closed end 20 incorporates a means for retention 45 enabling the female condom 10 to be held inside the vagina during sexual intercourse.

The means for retention 45 may be a diaphragm, a thin foam rubber disc or a ring made of a semi-rigid material or of foam rubber. It may be impregnated with a spermicidal and/or antiseptic substance.

The female condom 15 is made from a polymeric material such as natural rubber latex (NRL), polyethylene, polyurethane and derivatives and mixtures of these materials. The female condom 15 may be lubricated inside and/or outside with a lubricant sufficient to improve the comfort.

The female condom may be put in place just before coitus or even well before. Unlike the standard male condom, it is unnecessary to remove the female condom immediately after ejaculation.

What is claimed is:

1. A female condom for protection against transfer of sexually transmitted diseases, capable of being inserted into the vagina of a user, comprising:
   a. a flexible thin-walled tube having a closed end and an open end;
   b. said open end including means for stretching said open end radially;
   c. said radial stretching means comprising a collarette made of a material harder to the touch than said flexible thin tube, said collarette
      i. extending in a direction perpendicular to said tube in such a way as to cover the vulva during coitus, and,
      ii. having a protuberance elongated in the direction of the user's anus.

2. A female condom according to claim 1, wherein said means for stretching said open end radially comprises a ring having substantially the same diameter of said tube and delimiting said collarette with respect to said tube.

3. A female condom according to claim 2, wherein said collarette is a material more rigid than said tube.

4. The female condom of claim 2 wherein said collarette, flexible tube and ring are formed of a common stretchable material.

5. The female condom of claims 4 wherein the common stretchable material is a latex material.

6. A female condom according to claim 1, wherein said collarette is a material more rigid than said tube.

7. A female condom according to claim 1, wherein said collarette is thicker than said tube.

8. A female condom according to claim 1, wherein length of said is sufficient to maintain said collarette in contact with the vulva.

9. A female condom according to claim 1, wherein said closed end includes means for retaining said female condom inside the vagina during sexual intercourse.

10. A female condom according to claim 9, wherein said retention means is a disk made of semi-rigid material.

11. A female condom according to claim 10, wherein said retention means is impregnated with a spermicidal substance.

12. A female condom according to claim 1 further comprising means for fixing said retention means to said thin-walled tube.

13. A female condom according to claim 10, wherein said retention means is impregnated with an antiseptic substance.

14. A female condom according to claim 13 further comprising means for fixing said retention means to said thin-walled tube.

15. A female condom according to claim 10 further comprising means for fixing said retention means to said thin-walled tube.

16. A female condom according to claim 10 wherein said flexible thin-walled tube is made from a polymeric material selected from the group comprising natural rubber latex, polyethylene, polyurethane and derivatives and mixtures of said materials.

17. A female condom according to claim 9, wherein said retention means is insertable into said closed end in such a way that said retention means may be removed.

18. A female condom according to claim 9, wherein said retention means is a disk made of foam rubber.

19. A female condom according to claim 18, wherein said retention means is impregnated with a spermicidal substance.

20. A female condom according to claim 18, wherein said retention means is impregnated with an antiseptic substance.

21. A female condom according to claim 18 further comprising means for fixing said retention means to said thin-walled tube.

22. A female condom according to claim 18 wherein said flexible thin-walled tube is made from a polymeric material selected from the group comprising natural rubber latex, polyethylene, polyurethane and derivatives and mixtures of said materials.

23. A female condom according to claim 1 wherein said flexible thin-walled tube is made from a polymeric material selected from the group comprising natural rubber latex, polyethylene, polyurethane and derivatives and mixtures of said materials.

24. The female condom of claim 1 further comprising a ring which has a common diameter with that of the open end of the tube and said ring being formed with said collarette so as to provide a single piece female condom.

25. The female condom of claim 1 wherein said collarette defines a flexible peripheral flange extending circumferentially about the open end of said flexible tube to opposite sides of said tongue, with said tongue being an integral extension of said peripheral flange.

26. The female condom of claim 25 wherein said peripheral flange has a width of 1 to 4 cm.

27. The female condom of claim 25 wherein the width of said peripheral flange is uniform in extending continuously from one side of the tongue to an opposite side of said tongue.

28. The female condom of claim 1 wherein said collarette and flexible tube are formed of a common stretchable polymeric material.

29. The female condom of claim 28 wherein the common stretchable material is a latex material.

30. A female condom for protection against the transfer of sexually transmitted diseases capable of being inserted in the vagina of a user, the female condom comprising:

a flexible thin-walled tube having a closed end and an open end;

a collarette which extends about the open end of said tube so as to maintain an open end state in the open end of said tube, said collarette being of a material that is harder to touch than said flexible thin tube, said collarette extending in a direction perpendicular to said tube so as to cover the vulva during coitus, and said collarette having a tongue protuberance that is elongated in the direction of the user's anus, and said female condom being a single piece condom.

31. The female condom of claim 30 further comprising a ring which has a common diameter with that of the open end of the tube and said ring being formed with said collarette so as to provide a single piece female condom.

32. The female condom of claim 31 wherein said collarette defines a peripheral flange extending circumferentially about the open end of said flexible tube to opposite sides of said tongue.

33. The female condom of claims 31 wherein the single piece condom is formed of a common stretchable polymeric material.

34. The female condom of claim 33 wherein the single piece condom is formed entirely of latex stretchable material.

35. The female condom of claim 31 wherein at least one of said flexible tube, collarette and ring forming the single piece female condom is formed of a material different than another of said flexible tube, collarette and ring forming the single piece female condom.

36. The female condom of claim 30 wherein said collarette defines a peripheral flange extending circumferentially about the open end of said flexible tube to opposite sides of said tongue.

37. The female condom of claim 36 wherein said peripheral flange has a width of 1 to 4 cm.

38. The female condom of claim 37 wherein the width of said peripheral flange is uniform in extending continuously from one side of the tongue to an opposite side of said tongue.

39. The female condom of claim 37 wherein the peripheral flange has a width of 1 to 2 cm.

40. The female condom of claim 30 wherein said tongue has a radial length sufficient to cover a region lying between the vulva and anus during coitus.

41. The female condom of claim 30 wherein the female condom is a single piece condom formed of a polymeric material.

42. The female condom of claim 41 wherein the difference in hardness is achieved by a different thickness of a common material.

43. The female condom of claim 30 wherein said collarette defines a flexible peripheral flange extending circumferentially about the open end of said flexible tube to opposite sides of said tongue, with said tongue being an integral extension of said peripheral flange.

* * * * *